(12) United States Patent
Urai et al.

(10) Patent No.: US 11,957,143 B2
(45) Date of Patent: Apr. 16, 2024

(54) HIGHLY-SOLUBLE REBAUDIOSIDE D

(71) Applicant: SUNTORY HOLDINGS LIMITED, Osaka (JP)

(72) Inventors: Soichiro Urai, Kanagawa (JP); Yoshiaki Yokoo, Kanagawa (JP); Koji Nagao, Kanagawa (JP); Hiroshi Takiyama, Tokyo (JP); Shoji Kudo, Tokyo (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 837 days.

(21) Appl. No.: 16/976,874

(22) PCT Filed: Feb. 28, 2019

(86) PCT No.: PCT/JP2019/007753
§ 371 (c)(1),
(2) Date: Aug. 31, 2020

(87) PCT Pub. No.: WO2019/168082
PCT Pub. Date: Sep. 6, 2019

(65) Prior Publication Data
US 2020/0404955 A1 Dec. 31, 2020

(30) Foreign Application Priority Data

Mar. 1, 2018 (JP) ................. 2018-036638

(51) Int. Cl.
*A23L 27/30* (2016.01)
*C07H 15/256* (2006.01)

(52) U.S. Cl.
CPC ............ *A23L 27/30* (2016.08); *C07H 15/256* (2013.01)

(58) Field of Classification Search
None
See application file for complete search history.

(56) References Cited

U.S. PATENT DOCUMENTS

| | | |
|---|---|---|
| 2011/0104353 A1 | 5/2011 | Lee |
| 2013/0071339 A1 | 3/2013 | Markosyan |
| 2013/0251881 A1 | 9/2013 | Mutilangi et al. |
| 2013/0274351 A1 | 10/2013 | Markosyan et al. |
| 2014/0342043 A1 | 11/2014 | Bell et al. |
| 2014/0342044 A1 | 11/2014 | Bell et al. |
| 2018/0289042 A1 | 10/2018 | Bell et al. |
| 2018/0371002 A1 | 12/2018 | Zhu et al. |

FOREIGN PATENT DOCUMENTS

| | | |
|---|---|---|
| CN | 104159908 A | 11/2014 |
| EP | 2 482 676 | 10/2014 |
| JP | 2015-511498 | 4/2015 |
| JP | 2016-518143 | 6/2016 |
| JP | 2016-521974 | 7/2016 |
| WO | 2010/146463 | 12/2010 |
| WO | 2011/056834 | 5/2011 |
| WO | 2011/112892 | 9/2011 |
| WO | 2012/082587 | 6/2012 |
| WO | 2017/012572 | 1/2017 |

OTHER PUBLICATIONS

"Handbook of Organic Compounds crystallization-Principles and know-how-," edited by Hirayama Noriaki, Maruzen Inc., pp. 57-84, p. 62, lines 1-7, etc., non-official translation (Jul. 25, 2008).
International Search Report issued in PCT/JP2019/007753, dated May 28, 2019, along with an English-language translation.
Caira, M., "Crystalline Polymorphism of Organic Compounds" Topics in Current Chemistry, vol. 198, pp. 163-208 (1998).
Extended European Search Report issued in EP Patent Application No. 19761306.0, dated Nov. 3, 2021.
"Polymorphism in Pharmaceutical Solids", Brittain, H.G., Ed., Second Edition, 2009, pp. 333-339, in particular page 334.
Office Action issued in AU Patent Application No. 2019227764, dated Feb. 25, 2021.
Office Action issued in CN Patent Application No. 201980016012.4, dated Dec. 20, 2022, along with an English language translation.

*Primary Examiner* — Jyoti Chawla

(74) *Attorney, Agent, or Firm* — GREENBLUM & BERNSTEIN, P.L.C.

(57) ABSTRACT

The purpose of the present invention is to provide a crystal of rebaudioside D that exhibits high solubility in water. In one embodiment, the present invention provides a rebaudioside D crystal having a crystalline form α that shows peaks in X-ray diffraction (CuKα: λ=1.5405 Å) at two or more positions selected from the group consisting of 2θ=6.7±0.2 deg, 10.8±0.2 deg, 12.9±0.15 deg, and 22.2±0.2 deg.

6 Claims, 8 Drawing Sheets

FIGURE 1

| Name | R₁ | R₂ |
|---|---|---|
| Steviol | H | H |
| Steviolmonoside | H | Glc |
| Steviolbioside | H | Glc-Glc(β2→1) |
| Dulcoside A | Glc | Glc-Rha(β2→1) |
| Rubusoside | Glc | Glc |
| Stevioside | Glc | Glc-Glc(β2→1) |
| Rebaudioside A | Glc | Glc-Glc(β2→1)<br>\|<br>Glc(β3→1) |
| Rebaudioside B | H | Glc-Glc(β2→1)<br>\|<br>Glc(β3→1) |
| Rebaudioside C (Dulcoside B) | Glc | Glc-Rha(β2→1)<br>\|<br>Glc(β3→1) |
| Rebaudioside D | Glc-Glc(β2→1) | Glc-Glc(β2→1)<br>\|<br>Glc(β3→1) |
| Rebaudioside E | Glc-Glc(β2→1) | Glc-Glc(β2→1) |
| Rebaudioside F | Glc | Glc-Xyl(β2→1)<br>\|<br>Glc(β3→1) |

EXPERIMENT RESULTS FOR SOLUBILITY OF CRYSTALLINE FORM α (SHORT TERM)

A) TURBIDITY 40 MINUTES AFTER DISSOLUTION

B) AMOUNT DISSOLVED 40 MINUTES AFTER DISSOLUTION

FIGURE 8

EXPERIMENT RESULTS FOR SOLUBILITY OF CRYSTALLINE FORM α (LONG TERM)

A) AMOUNT DISSOLVED 24 H AFTER DISSOLUTION (mg/500 ml@7.5°C)

A) SCHEME FOR CONFIRMING ABILITY OF CRYSTALLINE FORM α TO IMPROVE SOLUBILITY

B) AMOUNT DISSOLVED

FIGURE 10

HIGHLY-SOLUBLE REBAUDIOSIDE D

TECHNICAL FIELD

The present invention relates to a crystal of rebaudioside D that is highly soluble in water and a method for producing the crystal. The present invention further relates to a sweetener composition containing the crystal of rebaudioside D and a food or beverage containing the sweetener composition.

BACKGROUND ART

The leaves of *Stevia rebaudiana* contain a secondary metabolite called steviol, which is a kind of diterpenoid, and steviol glycosides are used in the food industry as sweeteners with less calories since they are about 300 times sweeter than sugar. Obesity is developing internationally into a serious social problem, and the demand for sweeteners with less calories is increasing day by day also for promoting health and reducing medical cost. Currently, artificially synthesized amino acid derivatives such as aspartame and acesulfame potassium are used as artificial sweeteners, but naturally occurring sweeteners with less calories such as steviol glycosides are safer and thus expected to be easier to obtain the public acceptance.

Figure 1:
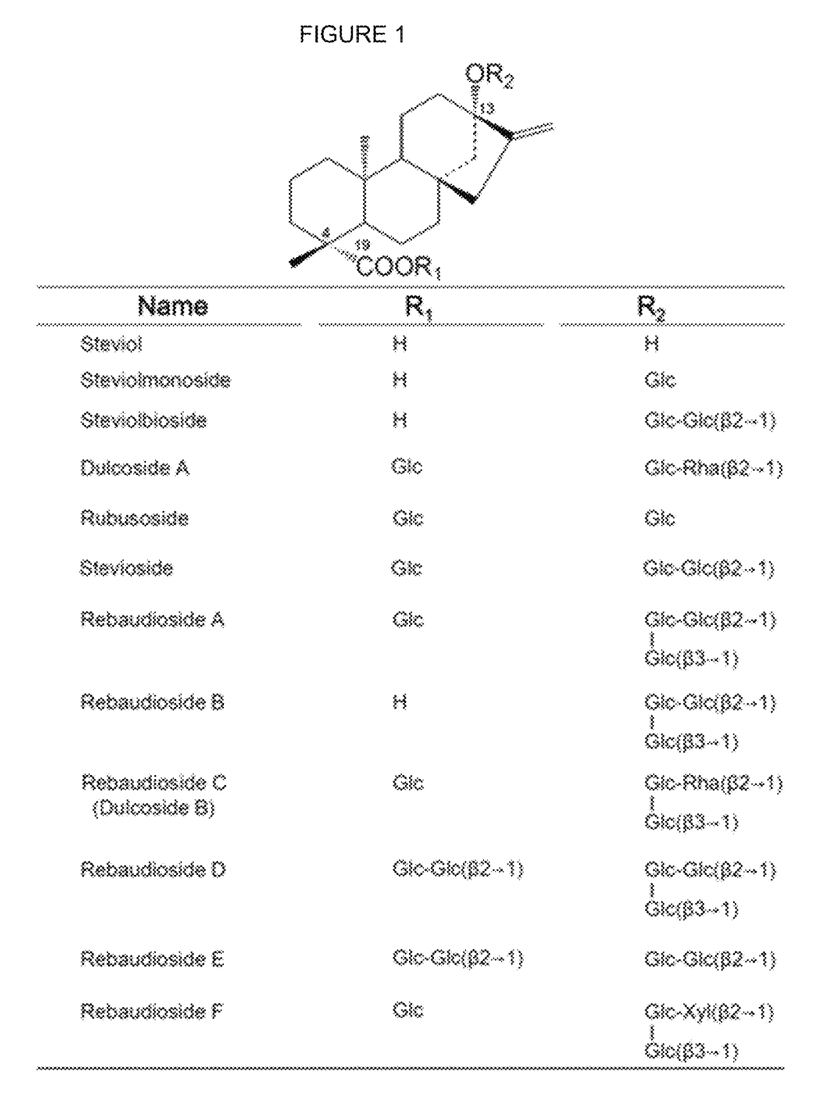
FIG. 1 shows a common structure and names of steviol glycosides.

FIG. 1 shows a common structure of steviol glycosides. The major steviol glycosides of *stevia* include a glycoside called Rebaudioside A (Reb. A) with four sugars attached. Its precursor called stevioside that is steviol triglycoside is the most abundant. These two are the central materials serving as sweeteners of *stevia*. It is known that stevioside is the most abundant in *stevia* leaves and is about 250 to 300 times sweeter than sugar. Reb. A is a steviol tetraglycoside having a high sweetness (200 to 450 times sweeter than sugar) and a good taste. These are attracting attention as sweeteners with less calories.

Rebaudioside D (Reb. D) has been attracting attention as a steviol glycoside having a further excellent taste than Reb. A. Reb. D has a structure with five sugars added to the diterpene skeleton shown in FIG. 1 and is about 200 to 300 times sweeter than sugar. Accordingly, attempts have been made to add rebaudioside D as a sweetener to beverages (for example, Patent Literatures 1 and 2) and to use it as a taste improver (for example, Patent Literature 3), so far.

CITATION LIST

Patent Literature

Patent Literature 1: Japanese Translation of PCT International Application Publication No. 2016-518143
Patent Literature 2: Japanese Translation of PCT International Application Publication No. 2016-521974
Patent Literature 3: European Patent No. 2482676

SUMMARY OF INVENTION

Technical Problem

However, since rebaudioside D has a low solubility in water as compared with rebaudioside A or the like, a problem of rebaudioside D is that it is difficult to add rebaudioside D at a concentration that provides a sufficient sweetness to foods and beverages. The present invention has been made to solve such a problem.

Accordingly, it is an object of the present invention to provide a crystal of rebaudioside D that is highly soluble in water.

Solution to Problem

As a result of dedicated studies to solve the aforementioned problem, the inventors have found crystalline forms of rebaudioside D that are highly soluble in water and a method for producing the crystalline forms. The present invention is based on this finding.

That is, the present invention has the following features.

[1] A crystal of rebaudioside D in a crystalline form α exhibiting peaks at at least two positions selected from the group consisting of 2θ=6.7±0.2 deg, 10.8±0.2 deg, 12.9±0.15 deg, and 22.2±0.2 deg, in X-ray diffraction (CuKα: λ=1.5405 Å).

[2] A crystal of rebaudioside D in a crystalline form β exhibiting peaks at at least two positions selected from 2θ=5.9±0.2 deg, 7.3±0.2 deg, 11.5±0.2 deg, and 16.8±0.2 deg, in X-ray diffraction (CuKα: λ=1.5405 Å).

[3] The crystal according to [1], further exhibiting a peak at at least one position selected from the group consisting of 2θ=6.3±0.2 deg, 8.9±0.2 deg, 10.3±0.2 deg, 14.4±0.2 deg, 17.4±0.2 deg, and 17.8±0.2 deg.

[4] The crystal according to [2], further exhibiting a peak at at least one position selected from the group consisting of 2θ=18.0±0.2 deg and 19.0±0.2 deg.

[5] The crystal according to any one of [1] to [4], having a moisture content of 0.1 wt % to 2.0 wt %.

[6] A sweetener composition comprising the crystal according to any one of [1] to [5].

[7] A food or beverage comprising the sweetener composition according to [6].

[8] The food or beverage according to [7], wherein the rebaudioside D is contained in the food or beverage in an amount of 10 mass ppm to 600 mass ppm.

Advantageous Effects of Invention

The present invention can provide a crystal of rebaudioside D that is highly soluble in water. The present invention can further provide a sweetener composition containing the crystal of rebaudioside D that is highly soluble in water and a food or beverage containing the sweetener composition.

DESCRIPTION OF EMBODIMENTS

Hereinafter, the present invention will be described in detail. The following embodiments are examples for explaining the present invention, and the present invention is not intended to be limited to the embodiments. The present invention can be implemented in various forms without departing from the gist thereof. All the documents and the patent literatures including publications, patent publications, and the like cited herein are incorporated hereinto as references.

The terms "rebaudioside" and "Reb." as used herein have the same meaning and all of them refer to "rebaudioside". Similarly, the term "dulcoside" as used herein refers to "dulcoside".

1. Crystal of Rebaudioside D

Rebaudioside D (Reb. D) has a structure of a diterpene skeleton with five sugars added shown in FIG. 1, as described above, and is specifically represented by the following formula.

Reb. D has a very high sweetness (about 200 to 300 times sweeter than sugar) and is superior in aftertaste or the like to generally distributed Reb. A. On the other hand, the solubility in water of Reb. A is about 10 to 20 g/500 ml at 7.5° C., whereas the solubility in water of currently commercially available Reb. D is about 0.2 to 0.25 g/500 ml. Therefore, it has been difficult to add Reb. D in a sufficient amount to bring sweetness to foods and beverages, despite having a more preferable taste than Reb. A.

Generally, Reb. D has a stable structure (which may be hereinafter referred to as "stable form") at normal temperature and pressure but has a problem of low solubility in water, as described above. Although details will be described later, a crystal of Reb. D of the present invention having improved solubility can be obtained by subjecting generally available Reb. D to a predetermined treatment.

The inventors have specified the crystal of rebaudioside D with a high solubility in water for the first time. The crystal of Reb. D of the present invention encompasses two types of crystalline forms. Among them, a crystalline form exhibiting peaks at at least two positions selected from the group consisting of $2\theta=6.7\pm0.2$ deg, $10.8\pm0.2$ deg, $12.9\pm0.15$ deg, and $22.2\pm0.2$ deg in the X-ray diffraction (CuKα: λ=1.5405 Å) is referred to as crystalline form α. Further, a crystalline form exhibiting peaks at at least two positions selected from $2\theta=5.9\pm0.2$ deg, $7.3\pm0.2$ deg, $11.5\pm0.2$ deg, and $16.8\pm0.2$ deg in the X-ray diffraction (CuKα: λ=1.5405 Å) is referred to as crystalline form β. The crystal in any of the crystalline forms has a high solubility in water. The solubility in water is preferably 0.20 g/500 ml or more, more preferably 0.25 g/500 ml or more, further preferably 0.28 g/500 ml or more, at 7.5° C. The upper limit of the solubility is preferably 0.33 g/500 ml or less, more preferably 0.32 g/500 ml or less, further preferably 0.31 g/500 ml or less, at 7.5° C. Alternatively, the upper limit may be 0.30 g/500 ml or less or 0.29 g/500 ml or less. The crystalline form α and the crystalline form β herein are metastable forms and may be referred to as Form α and Form β, respectively.

The crystal of Reb. D in the crystalline form α preferably exhibits peaks at at least three positions, more preferably peaks at four positions, selected from the group consisting of $2\theta=6.7\pm0.2$ deg, $10.8\pm0.2$ deg, $12.9\pm0.15$ deg, and $22.2\pm0.2$ deg in the X-ray diffraction (CuKα: λ=1.5405 Å). The crystal of Reb. D in the crystalline form α may further exhibit a peak at at least one position selected from the group consisting of $2\theta=6.3\pm0.2$ deg, $8.9\pm0.2$ deg, $10.3\pm0.2$ deg, $14.4\pm0.2$ deg, $17.4\pm0.2$ deg, and $17.8\pm0.2$ deg or may exhibit peaks at at least two positions, at least three positions, at least four positions, at least five positions, or at least six positions selected from this group.

The crystal of Reb. D in the crystalline form β preferably exhibits peaks at at least three positions, more preferably peaks at four positions selected from the group consisting of $2\theta=5.9\pm0.2$ deg, $7.3\pm0.2$ deg, $11.5\pm0.2$ deg, and $16.8\pm0.2$ deg in the X-ray diffraction (CuKα: λ=1.5405 Å). The crystal of Reb. D in the crystalline form β may further exhibit a peak at at least one position selected from the group consisting of $2\theta=18.0\pm0.2$ deg and $19.0\pm0.2$ deg or may exhibit peaks at two positions selected from this group.

As described above, the crystalline forms of the crystal of Reb. D of the present invention can be identified using an X-ray crystal diffraction (XRD). A generally available X-ray crystal diffractometer can be used therefor.

It can be said that when the difference of a peak position from a certain crystal peak is within ±0.2 deg, these peaks are deemed to be identical, but the difference is preferably within ±0.15 deg, more preferably within ±0.10 deg.

The crystal of Reb. D according to one aspect of the present invention not only has improved solubility itself but also can improve the solubility of a generally commercially available Reb. D having a low solubility when used in combination with the commercially available Reb. D. For example, to an aqueous solution in which a commercially available Reb. D has been dissolved therein to a saturated state, is added the crystal of Reb. D in the crystalline form α, thereby improving the solubility, and the crystal of Reb. D in the crystalline form α added later can be dissolved in the aqueous solution in the same manner and can be maintained without precipitation after that.

The Reb. D is not specifically limited and may be a plant-derived material, a chemical compound, or a biosynthetic product. For example, the Reb. D may be isolated and purified from a Reb. D-rich plant or may be obtained by chemical synthesis or biosynthesis.

The "solubility" herein means "the amount of solute dissolved in 500 ml of a solution with a liquid temperature of 7.5° C.", and its unit is [g/500 ml]. Unless otherwise specified herein, it refers to a solubility in a solution at 7.5° C.

The "moisture content" herein means the proportion of water contained in the crystal and is the proportion (wt %) of the weight of water based on the weight of the entire crystal. The moisture content of the crystal can be determined, for example, by heating the crystal at a high temperature (for example, 130° C.) under an inert atmosphere, and calculating from the change in weight between before and after the heating. The crystal of Reb. D of the present invention preferably has a moisture content of 0.1 wt % to 2.0 wt %, more preferably 0.2 wt % to 1.2 wt %, further preferably 0.40 wt % to 0.8 wt %.

The "turbidity (NTU)" herein means the degree of turbidity when the Reb. D is dissolved in water, and the lower the turbidity means that the Reb. D is dissolved better. The turbidity can be measured by a known method, for example, using an existing absorptiometer.

2. Sweetener Composition Containing Novel Steviol Glycoside

According to one aspect of the present invention, a sweetener composition containing the crystal of rebaudioside D in the crystalline form α or the crystalline form β (which may be hereinafter referred to as "the sweetener composition of the present invention") is provided. The sweetener composition of the present invention is not specifically limited, as long as it contains the crystal of rebaudioside D in the crystalline form α or the crystalline form β.

The amount of the glycoside of the present invention to be contained in the sweetener composition of the present invention is not specifically limited and is, for example, 50 to 100%, preferably 80 to 100%, more preferably 95 to 100%. The amount of the glycoside of the present invention to be contained in the sweetener composition of the present invention is the proportion (wt %) of the weight of the glycoside of the present invention based on the total weight of the sweetener composition.

The sweetener composition of the present invention may further contain other steviol glycosides. For example, the sweetener composition of the present invention may further contain one or more steviol glycosides selected from the group consisting of rebaudioside A, rebaudioside B, rebaudioside C, rebaudioside E, rebaudioside F, rebaudioside G, rebaudioside I, rebaudioside J, rebaudioside K, rebaudioside N, rebaudioside M, rebaudioside O, rebaudioside Q, rebaudioside R, rebaudioside V, rebaudioside W, rebaudioside KA, dulcoside A, rubusoside, steviol, steviol monoside, steviol bioside, and stevioside, in addition to the glycoside of the present invention.

In the case of containing such other steviol glycosides, the mass ratio of the glycoside of the present invention to the other steviol glycosides contained is preferably 50:50 to 100:0, more preferably 95:5 to 100:0.

The sweetener composition of the present invention may further contain general sweeteners. Examples of such general sweeteners include natural sweeteners such as fructose, sugar, fructose glucose liquid sugar, glucose, maltose, sucrose, high fructose syrup, sugar alcohol, oligosaccharide, honey, sugar cane juice (black molasses), starch syrup, Siraitia grosvenorii powder, Siraitia grosvenorii extract, licorice powder, licorice extract, Thaumatococcus daniellii seed powder, and Thaumatococcus daniellii seed extract, and artificial sweeteners such as acesulfame potassium, sucralose, neotame, aspartame, and saccharin. Among them, it is preferable to use natural sweeteners for imparting refreshing feeling, ease of drinking, natural taste, and appropriate rich taste, and it is particularly suitable to use fructose, glucose, maltose, sucrose, and sugar. Only one of these sweetening components may be used, or a plurality of them may be used.

Examples of the sweetener composition of the present invention include, but not limited to, tabletop functional sweetener compositions, syrups (concentrated solutions for beverages), sweetness enhancers, and flavor modifiers. In the case of using as a syrup, it may be diluted, for example, 2 to 5 times with water or the like for use in a beverage.

3. Food or Beverage Containing Sweetener Composition

According to one aspect of the present invention, a food or beverage containing the sweetener composition of the present invention (which may be hereinafter referred to as "the food or beverage of the present invention") is provided. The food or beverage of the present invention is not specifically limited, as long as it contains the sweetener composition of the present invention. Here, the "food or beverage" encompasses beverages and foods.

The amount of the Reb. D contained in the food or beverage of the present invention differs depending on the specific food or beverage but is preferably 10 mass ppm to 600 mass ppm, more preferably 10 mass ppm to 400 mass ppm, particularly preferably 10 mass ppm to 200 mass ppm. Adjusting the content to such a range is advantageous in that an appropriate sweetness can be imparted.

The food or beverage of the present invention may further contain other steviol glycosides. For example, the sweetener composition of the present invention may further contain one or more steviol glycosides selected from the group consisting of rebaudioside A, rebaudioside B, rebaudioside C, rebaudioside E, rebaudioside F, rebaudioside G, rebaudioside I, rebaudioside J, rebaudioside K, rebaudioside N, rebaudioside M, rebaudioside O, rebaudioside Q, rebaudioside R, rebaudioside V, rebaudioside W, rebaudioside KA, dulcoside A, rubusoside, steviol, steviol monoside, steviol bioside, and stevioside, in addition to the glycoside of the present invention.

In the case of containing such other steviol glycosides, the mass ratio of the rebaudioside D to the other steviol glycosides contained is preferably 50:50 to 100:0, more preferably 95:5 to 100:0.

The food or beverage of the present invention may further contain general sweeteners. Examples of such general sweeteners include natural sweeteners such as fructose, sugar, fructose glucose liquid sugar, glucose, maltose, sucrose, high fructose syrup, sugar alcohol, oligosaccharide, honey, sugar cane juice (black molasses), starch syrup, Siraitia grosvenorii powder, Siraitia grosvenorii extract, licorice powder, licorice extract, Thaumatococcus daniellii seed powder, and Thaumatococcus daniellii seed extract, and artificial sweeteners such as acesulfame potassium, sucralose, neotame, aspartame, and saccharin. Among them, it is preferable to use natural sweeteners for imparting refreshing feeling, ease of drinking, natural taste, and appropriate rich taste, and it is particularly suitable to use fructose, glucose, maltose, sucrose, and sugar. Only one of these sweetening components may be used, or a plurality of them may be used.

Examples of the food of the present invention include, but not specifically limited to, confectionery, breads, cereal flour, noodles, rice, processed agricultural and forest foods, processed livestock products, processed marine foods, milk and milk products, oils and fats/processed oils and fats, seasonings or other food materials.

Examples of the beverage of the present invention include, but not specifically limited to, carbonated beverages, non-carbonated beverages, alcohol beverages, non-alcohol beverages, coffee beverages, tea beverages, cocoa beverages, nutrition beverages, and functional beverages.

The beverage of the present invention may be prepared as a packaged beverage in the state of being heat sterilized and packed in a container. The container is not specifically limited and examples thereof can include PET bottles, aluminum cans, steel cans, paper packs, chilled cups, and bottles. In the case of performing heat sterilization, the type is not specifically limited, and a general technique such as UHT sterilization and retort sterilization, for example, can be used therefor. The temperature of the heat sterilization is not specifically limited and is, for example, 65 to 130° C., preferably 85 to 120° C., for 10 to 40 minutes. However, there is no problem even if sterilization is performed at a suitable temperature for several seconds such as 5 to 30 seconds, as long as a sterilization value equivalent to that in the aforementioned conditions is obtained.

4. Method for Producing Crystal of Rebaudioside D

As described above, the crystal of rebaudioside D of the present invention can be produced by heating or drying generally available Reb. D under predetermined conditions. Herein, "drying" may mean removing at least part of water contained in the target and does not necessarily include heating. For example, at least part of water contained in the target may be removed using a drying agent or by placing the target in vacuo.

The Reb. D used for producing the crystal of Reb. D of the present invention is not specifically limited and may be a plant-derived material, a chemical compound, or a biosynthetic product. For example, the Reb. D may be isolated and purified from a Reb. D-rich plant or may be obtained by chemical synthesis or biosynthesis.

Generally, the Reb. D is in a stable form at normal temperature and pressure, but the Reb. D in the crystalline form α or the crystalline form β can be obtained by heating the crystal of Reb. D at 40° C. to 150° C. for 0.5 hours to 5 hours.

According to one aspect of the present invention, the crystal of Reb. D in the stable form is converted into the crystalline form α at about 50° C. and converted into the crystalline form β at about 80° C., when it is heated in the atmospheric air at a rate of 2° C./rain.

The formation conditions of the crystalline form α and the crystalline form β can be confirmed, for example, using XRD-DSC combining an X-ray crystal diffractometer (XRD) with a differential scanning calorimeter (DSC).

The heating rate may be 900° C./hour to 750° C./hour, 750° C./hour to 225° C./hour, 225° C./hour to 150° C./hour, 150° C./hour to 60° C./hour, or 60° C./hour to 30° C./hour.

The heating may be performed in the atmospheric air or in an inert gas atmosphere such as nitrogen gas and argon gas.

The method for producing the crystal of Reb. D of the present invention preferably further includes maintaining the product in an inert gas atmosphere such as nitrogen gas and argon gas or in vacuo at 40° C. to 150° C. for 0.5 hours to 5 hours after heating. Such a step of maintaining in an inert gas atmosphere or in vacuo can prevent moisture absorption and enable efficient formation of a polymorph.

After heating, and maintaining at a predetermined temperature, if desired, the product may be cooled to normal temperature by natural cooling or using a cooler or the like at a cooling rate of 50° C./hour to 35° C./hour, 35° C./hour to 20° C./hour, 20° C./hour to 12° C./hour, 12° C./hour to 6.5° C./hour, 6.5° C./hour to 4.0° C./hour, or 4.0° C./hour to 2.0° C./hour.

After the completion of cooling, storage in vacuo or in an inert gas atmosphere is desirable. The storage in such a state can effectively prevent the crystalline form of the Reb. D from changing from the crystalline form α or the crystalline form β into a stable form having a low solubility.

EXAMPLES

Hereinafter, the present invention will be described further in detail by way of examples, but the contents of the present invention are not limited by these examples.

[Example 1] Preparation of Crystals of Reb. D in Crystalline Form α and Crystalline Form β

Rebaudioside D (RD: 95%) was heated under a nitrogen atmosphere to prepare crystals of Reb. D in the crystalline form α and the crystalline form β. At that time, an X-ray crystal diffractometer (XRD) ("model number: Ultima IV" manufactured by Rigaku Corporation) and a differential scanning calorimeter (DSC) ("model number: Thermo Plus2 system, XRD-DSCIII" manufactured by Rigaku Corporation) were used to measure endothermic reactions and exothermic reactions through changes in XRD pattern and changes in sample state during heating, thereby confirming that the crystalline form α and the crystalline form β were formed. The measurement conditions of each device are shown below. Regarding the measurement conditions of XRD (X-ray crystal diffraction), the same conditions were used in the subsequent examples.

XRD Measurement Conditions:
  2θ=5 to 35°
  Scan speed: 10°/min
DSC Measurement Conditions:
  Temperature increasing rate: 2° C./rain
  Heating temperature: 250° C.
  Atmosphere: nitrogen (100 mL/min)

Figure 2:
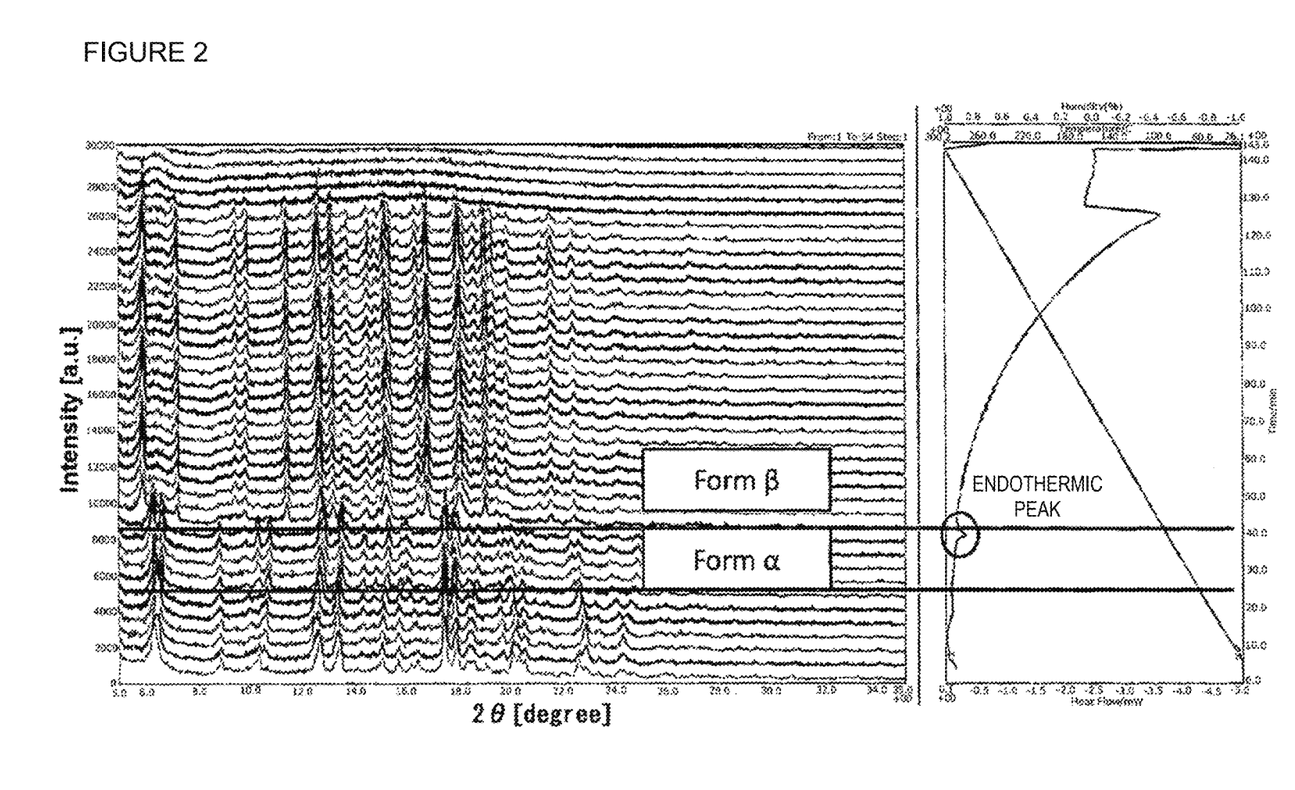
FIG. 2 include charts showing changes in the XRD and DSC patterns of Reb. D when a crystalline form α and a crystalline form β are formed.

FIG. 2 shows the measurement results. It was observed that, when the crystalline form α was formed, the peak in XRD was shifted into two in the temperature range of 50 to 65° C. at around 2θ=6.5°, and that when the crystalline form β was formed, the peaks in XRD further shifted in the range of 80 to 100° C. at around 2θ=6.0 to 7.5°.

[Example 2] Confirmation of Presence of Crystalline Forms α and β and Preparation of Crystals of Reb. D in Crystalline Forms α and β

Figure 3:
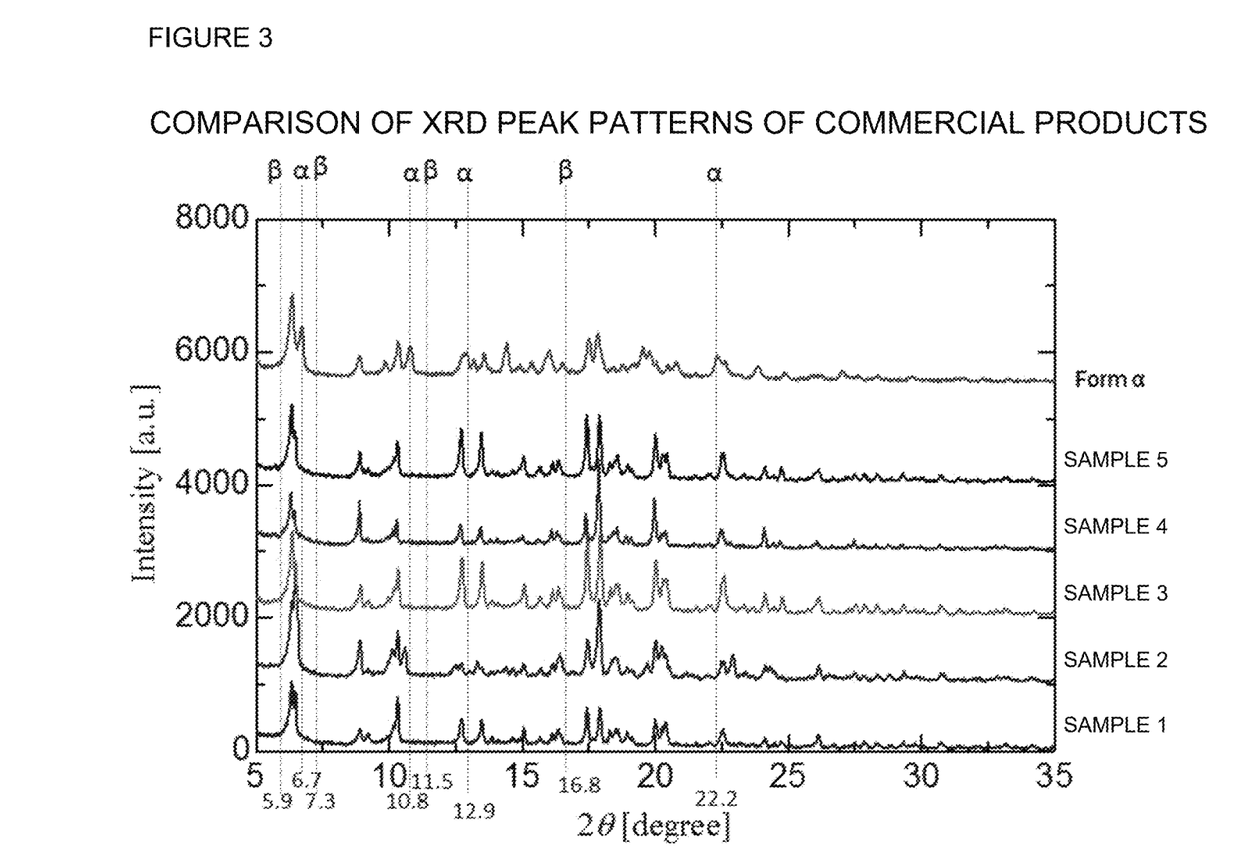
FIG. 3 is a chart showing the XRD patterns of five generally distributed and commercially available Reb. D products and the crystal of Reb. D in the crystalline form α.

Five generally distributed and commercially available products of Reb. D were subjected to X-ray crystal diffraction. Table 1 shows the samples used for the test, and FIG. 3 shows the XRD patterns obtained.

TABLE 1

| Sample | Sample name | Purity | Crystalline form α |
|---|---|---|---|
| 1 | JNRJ[1] | RD > 97% | No |
| 2 | Qufu Xiangzhou | RD > 95% | No |
| 3 | Layn | RD > 90% | No |
| 4 | GLG | RD > 95% | No |
| 5 | Lovpure natural | RD > 95% | No |

[1]JNRJ is an abbreviation for Jining Renewal & Joint International Co. Ltd.

It was confirmed from these results that the currently tested five generally distributed and commercially available products of Reb. D did not contain the crystals of Reb. D in the crystalline form α and the crystalline form β.

Figure 4:
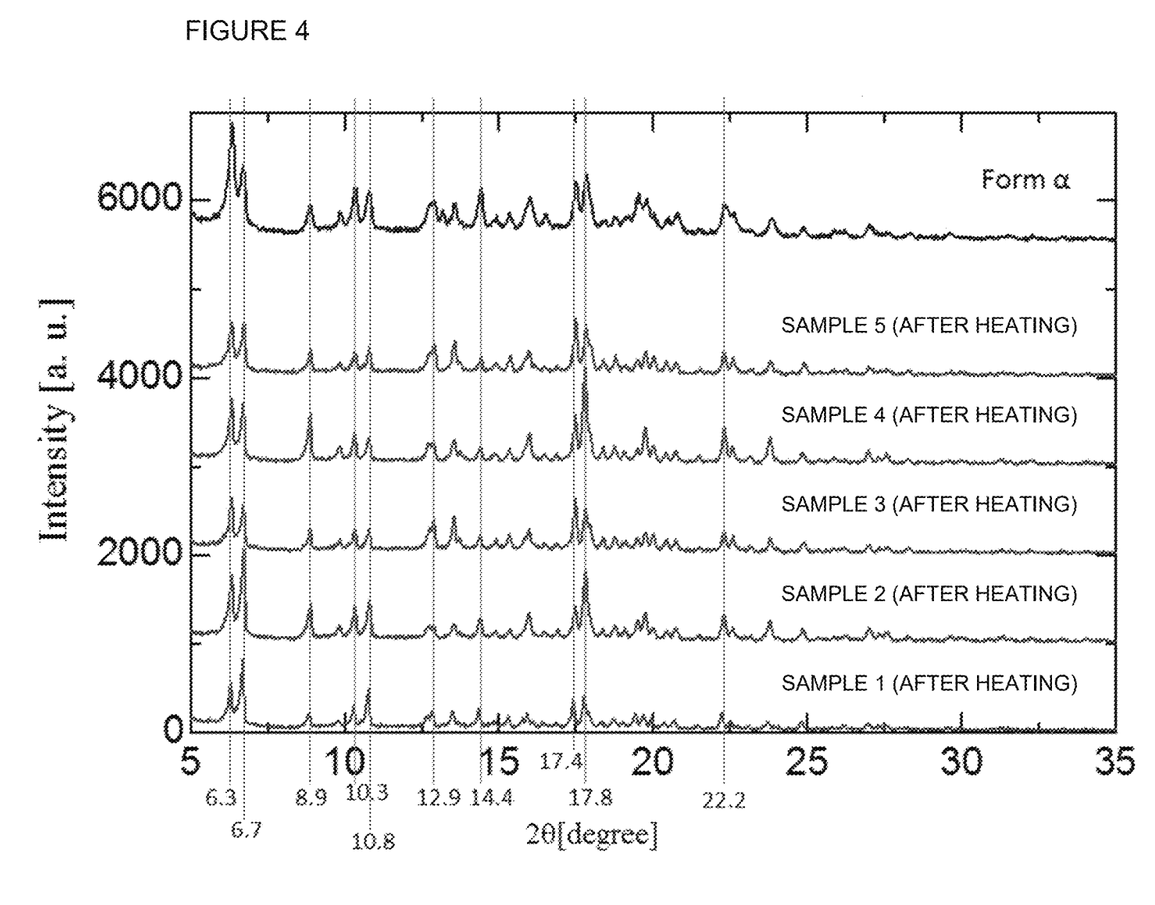
FIG. 4 is a chart showing the XRD patterns of five generally distributed and commercially available Reb. D products after conversion into the crystalline form α.

Then, samples 1 to 5 were heated to 50° C. in the same manner as in Example 1 to convert them into the crystalline form α, followed by X-ray crystal diffraction. FIG. 4 shows the XRD patterns obtained. It could be confirmed from these results that all samples 1 to 5 had the characteristic peaks of the crystalline form α.

Figure 5:
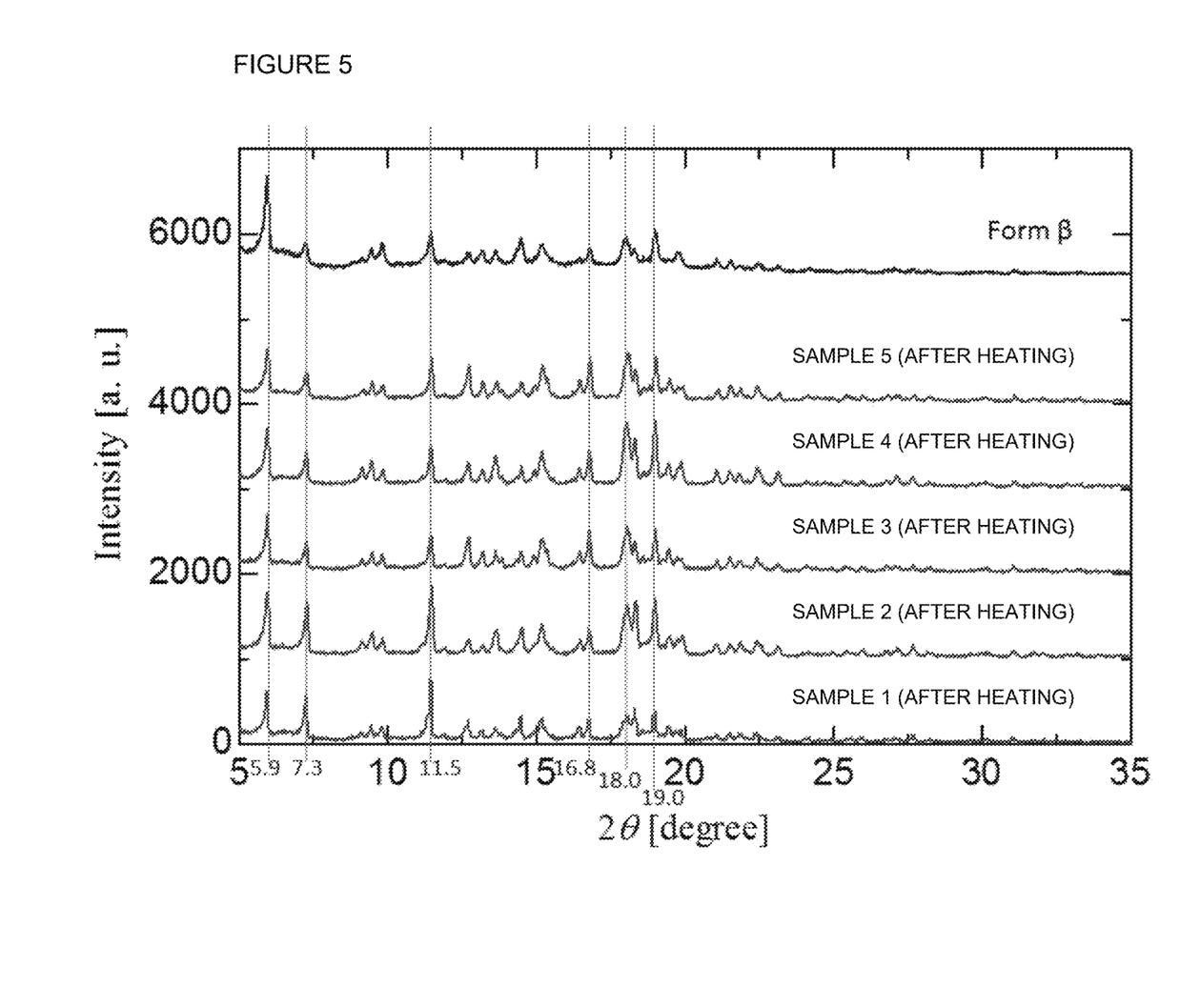
FIG. 5 is a chart showing the XRD patterns of five generally distributed and commercially available Reb. D products after conversion into the crystalline form β.

Further, samples 1 to 5 were continuously heated to 100° C. to convert them into the crystalline form β, followed by X-ray crystal diffraction. FIG. 5 shows the XRD patterns obtained. It could be confirmed from these results that all samples 1 to 5 had the characteristic peaks of the crystalline form β.

[Example 3] Solubility of Crystals of Reb. D

The crystals of Reb. D in the crystalline form α and the crystalline form β and a control (commercially available Reb. D in a stable form) were provided, to compare their solubilities. The crystal in the crystalline form α used was obtained by maintaining Reb. D at 50° C. for 1 hour, followed by appropriate $N_2$ purge, and the crystal in the crystalline form β used was obtained by maintaining Reb. D at 100° C. for 1.5 hours, followed by appropriate $N_2$ purge and then overnight cooling at normal temperature. The conditions for dissolution and sample preparation are shown below.

Dissolution Conditions:
300 mg of Reb. D was added to pure water (150 ml) at 7.5° C., followed by stirring at 200 rpm, for dissolution.

Sample Preparation Conditions:
A 0.45-um filter was immersed in the solution for 30 seconds, and then a filtrate was obtained through the filter. 1 ml of the filtrate obtained was collected and diluted 10-fold with pure water.

Figure 6:
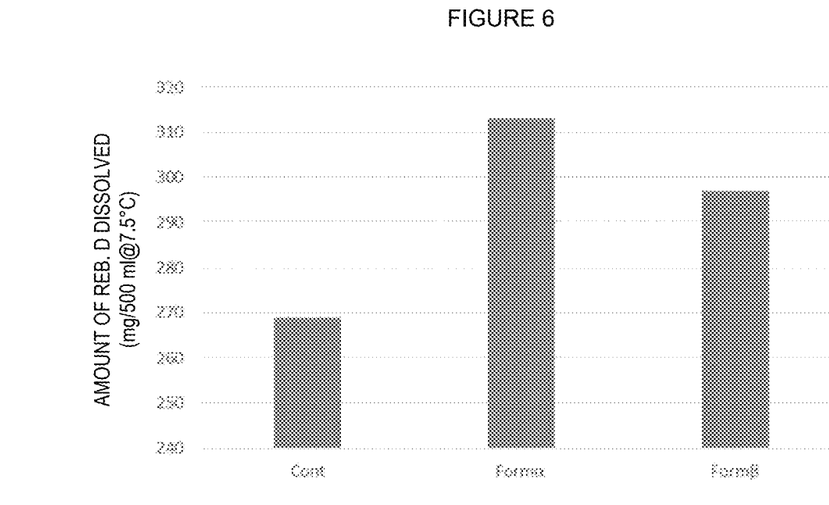
FIG. 6 is a graph comparing the solubilities in water of the crystalline form α, the crystalline form β, and the crystal of Reb. D as a control.

FIG. 6 shows the measurement results. It was observed that the amount dissolved increased in both of the crystals in the crystalline form α and the crystalline form β as compared with that in the control (Cont).

Then, the solubilities were evaluated under the conditions varied. The crystal in the crystalline form α used was obtained by maintaining at 55° C. for 2 hours, followed by appropriate $N_2$ purge and then natural cooling in vacuo. The dissolution conditions, the conditions of turbidity (NTU) measurement, and the sample preparation conditions are shown below.

Dissolution Conditions:
90 mg of Reb. D was added to 150 ml of pure water (equivalent to 300 mg/500 ml) at 7.5° C., followed by stirring at 350 rpm for dissolution. The degree of dissolution was checked 40 minutes later.

Conditions of Turbidity (NTU) Measurement:
30 ml was collected 40 minutes later, and the turbidity (NTU) was measured. The turbidity was measured with an absorptiometer (2100AN, manufactured by Hach Company) by turbidimetry using formazin as a standard solution.

Sample Preparation Conditions:
A 0.45-um filter was immersed in the solution for 6 seconds, and then a filtrate was obtained through the filter. 1 ml of the filtrate obtained was collected and diluted 10-fold with pure water.

Figure 7:
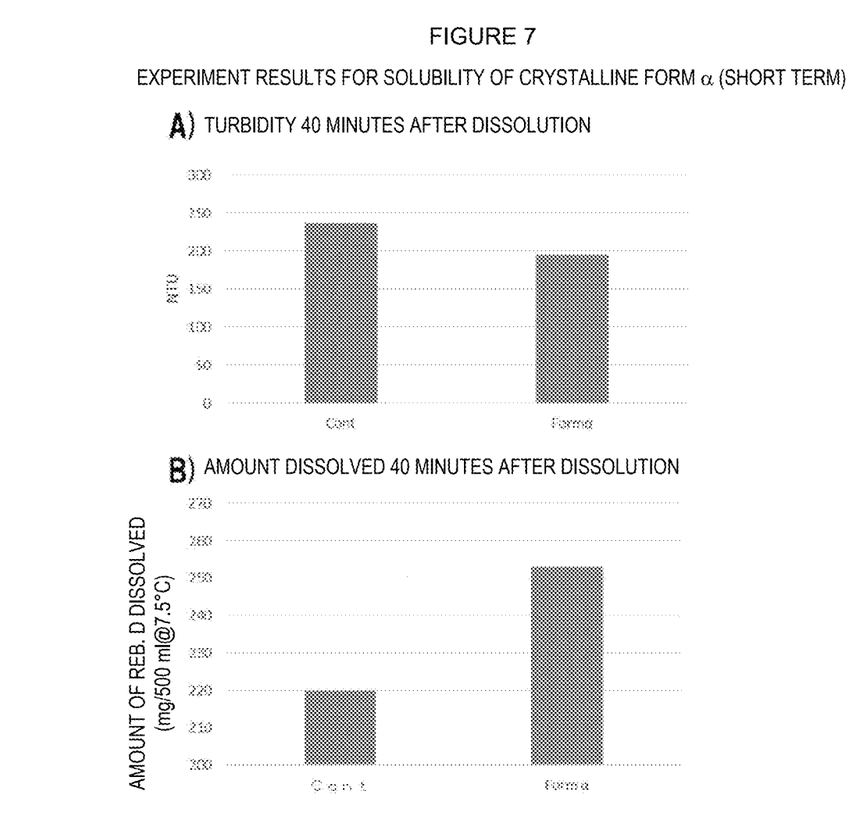
In FIG. 7, graph A is a graph showing the turbidities of the crystalline form α and the crystal of Reb. D as a control 40 minutes after dissolution. Graph B is a graph showing the amount dissolved at the same time.

FIG. 7 shows the measurement results. The turbidity tended to be low in the crystalline form α, suggesting that the solubilities were improved. It was also found that the amount dissolved also tended to increase.

Tests were further conducted to confirm the long-term solubilities. The crystal in the crystalline form α used was obtained by maintaining at 50° C. for 2 hours, followed by appropriate $N_2$ purge, and then standing in vacuo without heat retention, and the crystal in the crystalline form β used was obtained by maintaining at 100° C. for 2.0 hours, followed by appropriate $N_2$ purge, and then standing in vacuo without heat retention. The conditions for dissolution and sample preparation are shown below.

Dissolution Conditions:
300 mg of Reb. D was added to pure water (150 ml) at 7.5, followed by stirring at 200 rpm, for dissolution.

Sample Preparation Conditions:
A 0.2-um filter was immersed in the solution for 30 seconds, and then a filtrate was obtained through the filter. 1 ml of the filtrate obtained was collected and diluted 10-fold with pure water. This operation was repeated 3 times for each sample.

Figure 8:
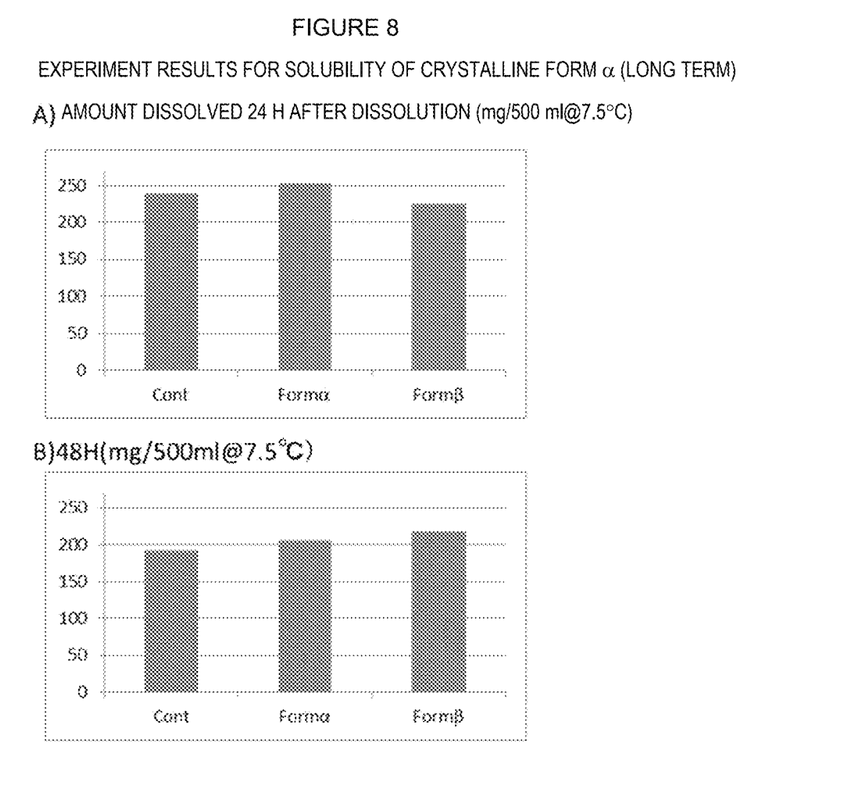
FIG. 8 includes graphs comparing the solubilities in water of the crystalline form α, the crystalline form β, and the crystal of Reb. D as a control. Graph A shows the amount dissolved 24 hours later. Graph B shows the amount dissolved 48 hours later.

FIG. 8 shows the measurement results. It was observed that the amount dissolved increased by about 5% in both crystals 24 hours and 48 hours after the dissolution as compared with that in the control (Cont).

Figure 9:
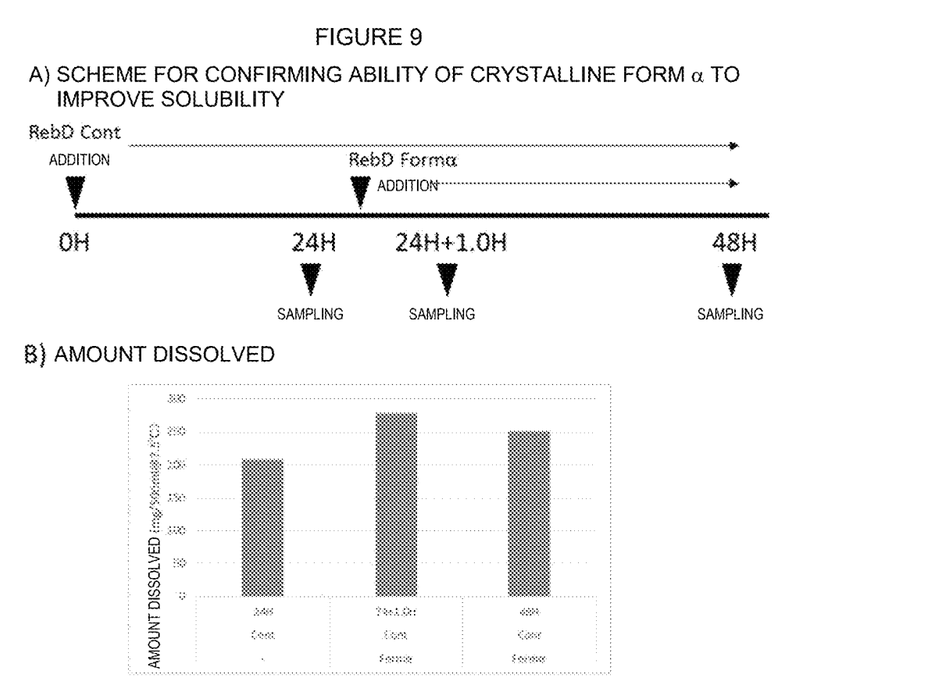
FIG. 9 includes diagrams for confirming that the solubility is improved by the crystal of Reb. D in the crystalline form α. Diagram A shows a scheme for confirming the ability of the crystalline form α to improve the solubility. Diagram B shows the amount dissolved.

[Example 4] Improvement in Solubility by Supplementary Addition of Crystal of Reb. D Using the Reb. D in the crystalline form α, tests were conducted to confirm that the solubility of commercially available Reb. D was improved. FIG. 9A shows a scheme to confirm the ability of the crystalline form α to improve the solubility. First, commercially available Reb. D (in a stable form) was added to water to a saturated state. 24 hours later, the crystal of Reb. D in the crystalline form α was added to the saturated solution. Sampling was performed 24 hours later, 25 hours later, and 48 hours later, to check the amount of the Reb. D dissolved. FIG. 9B shows the results. The amount dissolved further increased by addition of the crystal of Reb. D in the crystalline form α to the solution in the saturated state, and the increase continued 24 hours after the crystal of Reb. D in the crystalline form α was added.

[Example 5] Comparison of Moisture Contents of Crystalline Forms

Figure 10:
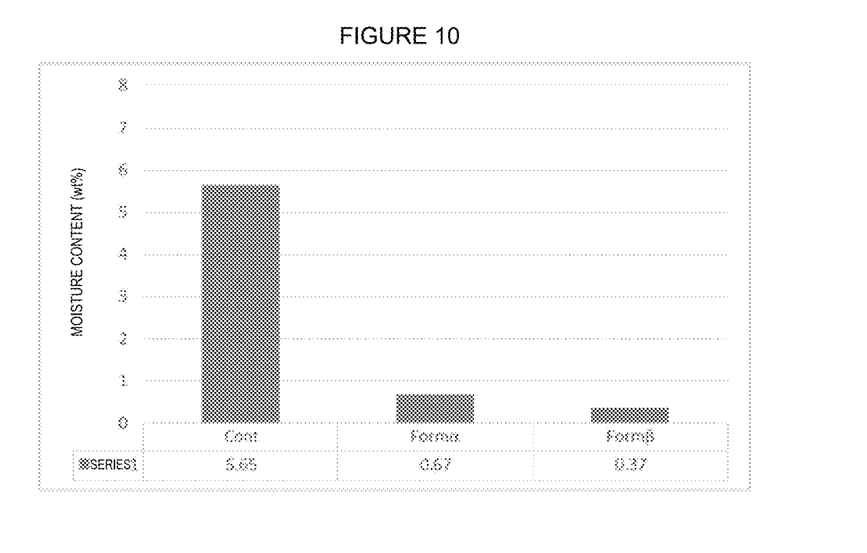
FIG. 10 is a graph comparing the moisture contents of the crystalline form α, the crystalline form β, and the crystal of Reb. D as a control.

The crystals of Reb. D in the crystalline form α and the crystalline form β and the control (in a stable form) were provided, and their moisture contents were compared. FIG. 10 shows the results. The devices and the conditions used for measuring the moisture contents are shown below.

Devices:

Trace moisture analyzer: CA-200, manufactured by Mitsubishi Chemical Analytech Co., Ltd.

Water vaporizer: VA-200

Reagents: AQUAMICRON AX as anolyte and AQUAMICRON CXU as catholyte

Sample heating: 130° C. in an inert gas atmosphere (gas: $N_2$, flow rate: 300 ml/min)

The moisture contents of the crystals in the respective crystalline forms were compared. As a result, the moisture content of the crystal as the control was over 5 wt %, which was highest. On the other hand, the moisture contents of the crystals in the crystalline form α and the crystalline form β were 0.67 wt % and 0.37 wt %, respectively. Unexpectedly, it turned out that the crystal in the crystalline form α with a higher solubility had a higher moisture content than the crystal in the crystalline form β.

The invention claimed is:

1. A crystal of rebaudioside D in a crystalline form α exhibiting peaks at at least two positions selected from the group consisting of 2θ=6.7±0.2 deg, 10.8±0.2 deg, 12.9±0.15 deg, and 22.2±0.2 deg, in X-ray diffraction (CuKα: λ=1.5405 Å).

2. The crystal according to claim 1, further exhibiting a peak at at least one position selected from the group consisting of 2θ=6.3±0.2 deg, 8.9±0.2 deg, 10.3±0.2 deg, 14.4±0.2 deg, 17.4±0.2 deg, and 17.8±0.2 deg.

3. The crystal according to claim 1, having a moisture content of 0.1 wt % to 2.0 wt %.

4. A sweetener composition comprising the crystal according to claim 1.

5. A food or beverage comprising the sweetener composition according to claim 4.

6. The food or beverage according to claim 5, wherein the rebaudioside D is contained in the food or beverage in an amount of 10 mass ppm to 600 mass ppm.

* * * * *